(12) United States Patent
Le et al.

(10) Patent No.: US 8,443,651 B2
(45) Date of Patent: May 21, 2013

(54) DROP TEST DEVICE FOR TESTING CORNER OF CASE

(75) Inventors: Yin Le, Shenzhen (CN); Yu-Lin Liu, Shenzhen (CN); Qiang Zhang, Shenzhen (CN)

(73) Assignees: Hong Fu Precision Industry (ShenZhen) Co., Ltd., Shenzhen (CN); Hon Hai Precision Industry Co., Ltd., New Taipei (TW)

( * ) Notice: Subject to any disclaimer, the term of this patent is extended or adjusted under 35 U.S.C. 154(b) by 277 days.

(21) Appl. No.: 12/978,130

(22) Filed: Dec. 23, 2010

(65) Prior Publication Data

US 2012/0024039 A1   Feb. 2, 2012

(30) Foreign Application Priority Data

Jul. 29, 2010   (CN) .......................... 2010 1 0240072

(51) Int. Cl.
*G01N 3/30* (2006.01)

(52) U.S. Cl.
USPC ........................................ 73/12.06; 73/12.14

(58) Field of Classification Search
USPC .................. 73/12, 6, 12.13–12.14, 12.06
See application file for complete search history.

(56) References Cited

U.S. PATENT DOCUMENTS

| | | | | |
|---|---|---|---|---|
| 5,214,954 | A * | 6/1993 | Abbott et al. ................. | 73/12.01 |
| 6,807,841 | B1 * | 10/2004 | Chen et al. .................... | 73/12.06 |
| 7,243,526 | B2 * | 7/2007 | Pringle ......................... | 73/12.09 |
| 7,900,499 | B2 * | 3/2011 | Zhang ........................... | 73/12.13 |
| 2004/0103713 | A1 * | 6/2004 | Voon et al. .................... | 73/12.04 |
| 2012/0024040 | A1 * | 2/2012 | Le et al. ........................ | 73/12.06 |

* cited by examiner

*Primary Examiner* — Max Noori
(74) *Attorney, Agent, or Firm* — Altis Law Group, Inc.

(57) ABSTRACT

A drop test device for testing a corner portion of a work piece, includes a bottom board, a support pillar, and a hanging mechanism. The support pillar is mounted on the bottom board. The hanging mechanism is mounted on the support pillar and is located above the bottom board. The hanging mechanism includes a support member. The support member includes a triangle base. Angles and sides of the triangle base hold the work piece thereon to have a corner of the work piece directed towards the bottom board.

8 Claims, 2 Drawing Sheets

DROP TEST DEVICE FOR TESTING CORNER OF CASE

BACKGROUND

1. Technical Field

The present disclosure relates to drop test devices, and particularly to a drop test device for testing the strength of a corner portion of a plate.

2. Description of Related Art

Various electronic apparatuses, such as computers, are contained in a metal case. For example, a computer system is generally received in a computer enclosure, which is usually made of steel plates. When the computer enclosure is being transported, the computer enclosure may be dropped because of carelessness. Corners of a plate are the most vulnerable portions. When a corner of a plate of a computer enclosure lands first, the corner is easily deformed and the computer system is damaged. Therefore, the corner of the plate should be strong enough to avoid deformation. It is needed to test the strength of the corners of the plate, which houses the computer enclosure to assure the corners are strong enough. However, it is not easy to test the strength of the corners because it is difficult to position the plate to have the corner land first when the plate drops.

Therefore, there is room for improvement within the art.

BRIEF DESCRIPTION OF THE DRAWINGS

Many aspects of the embodiments can be better understood with references to the following drawings. The components in the drawings are not necessarily drawn to scale, the emphasis instead being placed upon clearly illustrating the principles of the embodiments. Moreover, in the drawings, like reference numerals designate corresponding parts throughout the several views.

DETAILED DESCRIPTION

The disclosure is illustrated by way of example and not by way of limitation in the figures of the accompanying drawings in which like references indicate similar elements. It should be noted that references to "an" or "one" embodiment in this disclosure are not necessarily to the same embodiment, and such references mean at least one.

Figure 1:
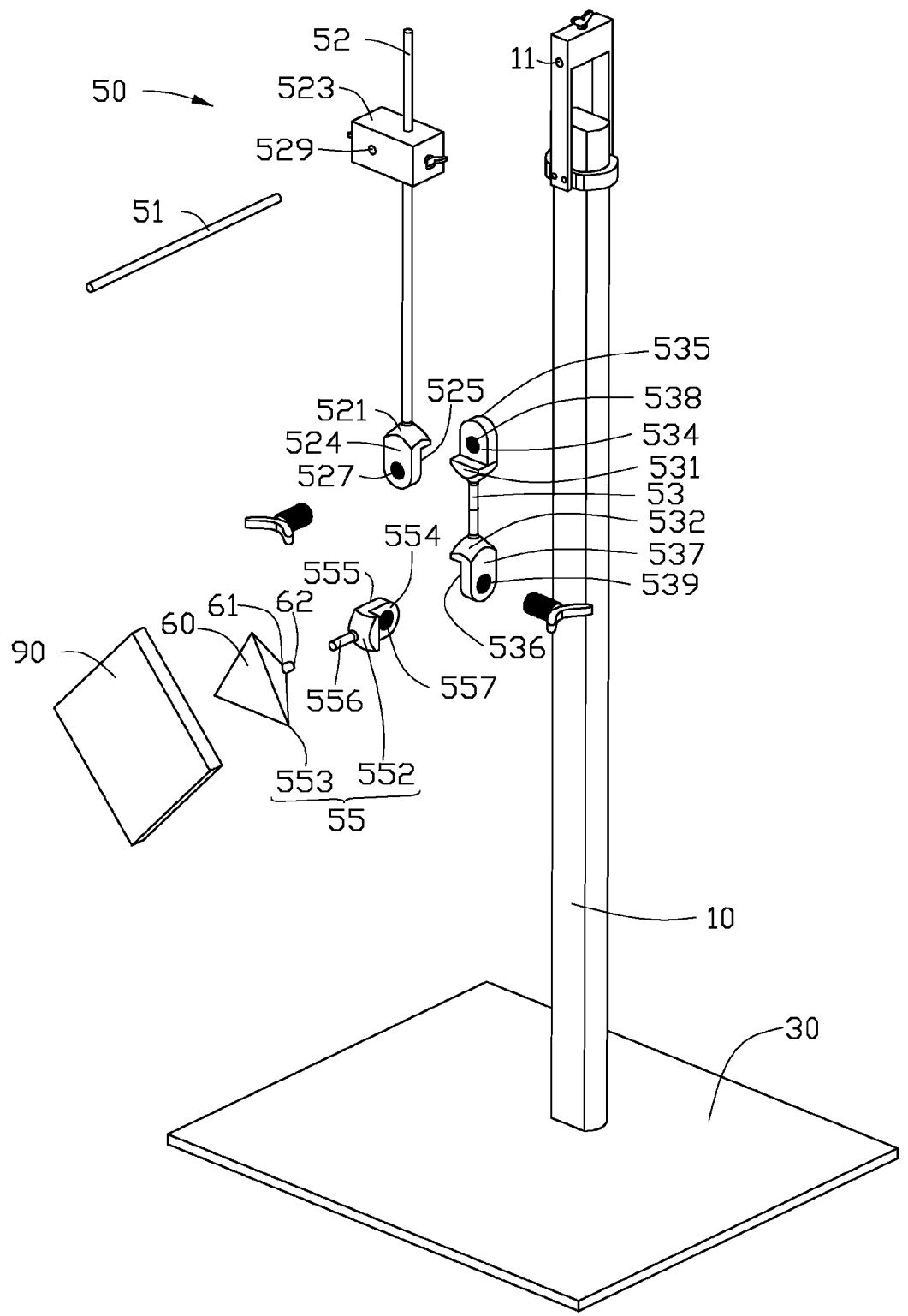
FIG. 1 is an isometric and exploded view of a drop test device in accordance with one embodiment.

Referring to FIG. 1, a drop test device in accordance with an embodiment includes a support pillar 10, a bottom board 30, and a hanging mechanism 50. The support pillar 10 is secured on the bottom board 30. The hanging mechanism 50 is configured to be mounted on the support pillar 10 and located above the bottom board 30.

The hanging mechanism 50 includes a horizontal first connection pole 51, an upright second connection pole 52, an upright third connection pole 53, and a support apparatus 55. The hanging mechanism 50 is configured to hang a work piece 90 thereon to test the strength of a corner of the work piece 90.

The support pillar 10 defines a securing hole 11, which extends in the horizontal direction. The first connection pole 51 is mounted in the securing hole 11.

The second connection pole 52 has a connection block 523 secured thereon. The connection block 523 defines a through hole 529, which extends in the horizontal direction. A lower portion of the second connection pole 52 forms a first connection portion 521 thereon. The first connection portion 521 includes a first side 524 and a second side 525. The first side 524 and the second side 525 are opposite to and parallel with each other. A first pivot hole 527 extends from the first side 524 to the second side 525.

The third connection pole 53 is a vertical pole. A second connection portion 531 is connected to an upper portion of the third connection pole 53. A third connection portion 532 is connected to a lower portion of the third connection pole 53. The second connection portion 531 includes a third side 534 and a fourth side 535. The third side 534 and the fourth side 535 are opposite to and substantially parallel with each other. The fourth side 535 is substantially parallel to the first side 524. A second pivot hole 538 extends from the fourth side 535 to the third side 534. The third connection portion 532 includes a fifth side 536 and a sixth side 537. The fifth side 536 and the sixth side 537 are opposite to and substantially parallel with each other. The fifth side 536 is perpendicular to the third side 534. A third pivot hole 539 extends from the fifth side 536 to the sixth side 537.

The support apparatus 55 includes a fourth connection member 552 and a support member 553. The fourth connection member 552 includes a seventh side 554 and an eighth side 555. The seventh side 554 and the eighth side 555 are opposite to and substantially parallel with each other. The seventh side 554 is substantially parallel to the fifth side 536. A fourth pivot hole 557 extends from the seventh side 554 to the eighth side 555. An end of the fourth connection member 552 has a first conjunction rod 556. A plurality of screw threads is located on the first conjunction rod 556. The support member 553 is a triangular pyramid, which includes a base 60 and an apex 61. A second conjunction rod 62 is connected to the apex 61. The second conjunction rod 62 defines a screw hole (not shown). The base 60 is a triangle, which includes three angles and three sides.

Figure 2:
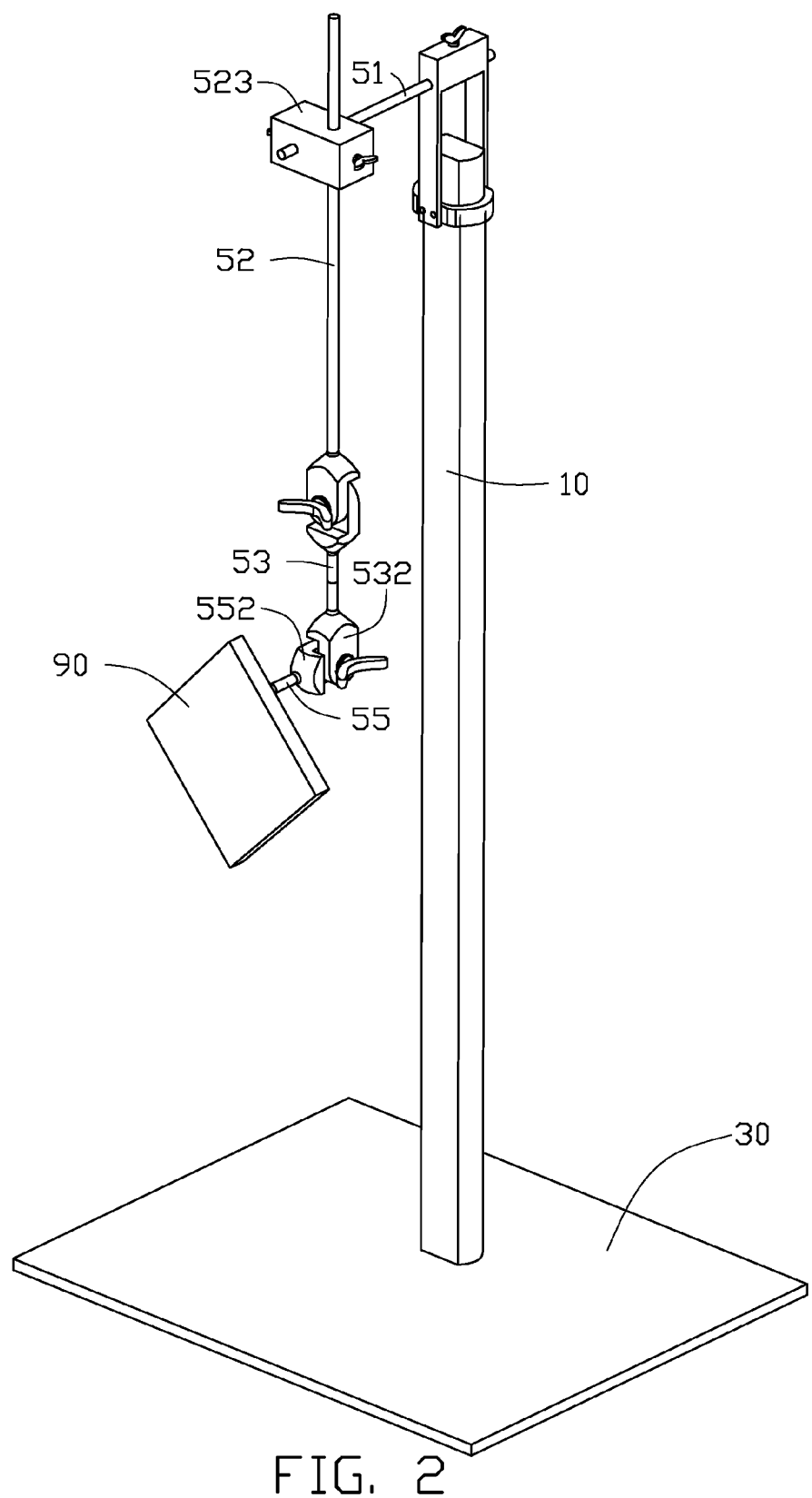
FIG. 2 is an assembled view of the drop test device of FIG. 1.

Referring to FIGS. 1 and 2, in assembly of the drop test device, the first connection pole 51 is inserted through the through hole 529, and mounted in the securing hole 11. The third side 534 of the second connection portion 531 is jointed to the second side 525 of the first connection portion 521. The first pivot hole 527 is in alignment with the second pivot hole 538. A first shaft is mounted in the first pivot hole 527 and second pivot hole 538 to pivotally mount the first connection portion 521 and the second connection portion 531 together.

Then, the fifth side 536 of the third connection portion 532 is jointed to the seventh side 554 of the fourth connection member 552. The third pivot hole 539 is in alignment with the fourth pivot hole 557. A second shaft is mounted in the third pivot hole 539 and the second connection portion 531 to pivotally mount the third connection portion 532 and the fourth connection member 552 together. The first conjunction rod 556 of the fourth connection member 552 is then mounted in the screw hole of the second conjunction rod 62. The support member 553 is configured to rotate around the first conjunction rod 556 to adjust the base 60.

To use the drop test device to test the work piece 90, the work piece 90 is hung on an angle or a side of the base 60 to make a corner of the work piece 90 directed towards the bottom board 30. The fourth connection member 552 is rotated quickly to release the work piece 90 from the base 60. The work piece 90 drops. A corner of the work piece 90 strikes on the bottom board 30. Therefore, the drop test device conveniently tests corners of the work piece 90.

In the drop test device, the first connection portion 521 and the second connection portion 531 are able to rotate with respect to each other. The third connection portion 532 and the fourth connection member 552 are able to rotate with respect to each other. Thus, a position of the work piece 90 is adjusted conveniently. Further, the connection block 523 can slide on the first connection pole 51 to move the work piece 90. Therefore, the work piece 90 can land on surfaces other than the bottom board 30.

It is to be understood, however, that even though numerous characteristics and advantages of the embodiments have been set forth in the foregoing description, together with details of the structure and function of the embodiments, the disclosure is illustrative only, and changes may be made in detail, especially in matters of shape, size, and arrangement of parts within the principles of the present disclosure to the full extent indicated by the broad general meaning of the terms in which the appended claims are expressed.

What is claimed is:

1. A drop test device for testing a corner portion of a work piece, the drop test device comprising:
   a bottom board;
   a support pillar mounted on the bottom board;
   a hanging mechanism mounted on the support pillar and located above the bottom board, the hanging mechanism comprising a support member, the support member comprising a triangle base, wherein angles and sides of the triangle base are configured to hang the work piece thereon to have a corner of the work piece directed towards the bottom board;
   wherein the hanging mechanism comprises a first connection pole, the first connection pole is horizontally mounted on the support pillar and located above the bottom board; the hanging mechanism comprises a second connection pole which extends vertically, a connection block is secured on the second connection pole, the connection block defines a through hole, and the first connection pole is inserted in the through hole to mount the second connection pole on the first connection pole; a second lower portion of the second connection pole has a first connection portion, the first connection portion comprises a first side and a second side, and the first side and the second side are opposite to and parallel with each other; a first pivot hole extends between the first side and the second side; the hanging mechanism comprises a third connection pole, a third upper portion of the third connection pole has a second connection portion, the second connection portion comprises a third side and a fourth side, and a second pivot hole extends between the third side and the fourth side; and the third side is jointed to the second side, the first pivot hole is in alignment with the second pivot hole, and a first shaft is pivotally mounted in the first pivot hole and the second pivot hole.

2. The drop test device of claim 1, wherein a third lower portion of the third connection pole has a third connection portion, the third connection portion comprises a fifth side and a sixth side, the fifth side and the sixth side are opposite to and parallel with each other, and the fifth side is perpendicular to the third side.

3. The drop test device of claim 2, wherein a third pivot hole extends between the fifth side and the sixth side; the hanging mechanism comprises a fourth connection member, the fourth connection member comprises a seventh side and an eighth side, the seventh side and the eighth side are opposite to and parallel with each other, the seventh side is parallel to the fifth side, and a fourth pivot hole extends between the seventh side and the eighth side; and the third pivot hole is in alignment with the fourth pivot hole, and a second shaft is pivotally mounted in the third pivot hole and the fourth pivot hole.

4. The drop test device of claim 3, wherein a first conjunction rod is connected to an end of the fourth connection member, a plurality of screw threads are defined on the first conjunction rod; the support member comprises a triangular pyramid which comprises an apex, the triangle base is located on the triangular pyramid, a second conjunction rod is connected to the apex, the second conjunction rod defines a screw hole, and the first conjunction rod is rotatably mounted in the screw hole.

5. A drop test device for testing a corner portion of a work piece, the drop test device comprising:
   a bottom board having a support pillar vertically mounted on the bottom board;
   a first connection pole mounted on the support pillar substantially in the horizontal plane;
   a support apparatus pivotally mounted on the first connection pole and located above the bottom board, the support apparatus comprising a support member, the support member comprising a triangle base, wherein angles and sides of the triangle base are configured to hang the work piece thereon to have a corner of the work piece directed towards the bottom board; and
   a second connection pole which extends vertically, wherein a connection block is secured on the second connection pole, the connection block defines a through hole, and the first connection pole is inserted in the through hole to mount the second connection pole on the first connection pole; a second lower portion of the second connection pole has a first connection portion, the first connection portion comprises a first side and a second side, and the first side and the second side are opposite to and parallel with each other, a first pivot hole extends between the first side and the second side; a third upper portion of a third connection pole has a second connection portion, the second connection portion comprises a third side and a fourth side, a second pivot hole is defined between the third side and the fourth side; and the third side is jointed to the second side, the first pivot hole is in alignment with the second pivot hole, and a first shaft is pivotally mounted in the first pivot hole and the second pivot hole.

6. The drop test device of claim 5, wherein a third lower portion of the third connection pole has a third connection portion, the third connection portion comprises a fifth side and a sixth side, the fifth side and the sixth side are opposite to and parallel with each other, and the fifth side is perpendicular to the third side.

7. The drop test device of claim 6, wherein a third pivot hole extends between the fifth side and the sixth side; a fourth connection member comprises a seventh side and an eighth side, the seventh side and the eighth side are opposite to and parallel with each other, the seventh side is parallel to the fifth side, and a fourth pivot hole extends between the seventh side and the eighth side; the third pivot hole is in alignment with the fourth pivot hole, and a second shaft is pivotally mounted in the third pivot hole and the fourth pivot hole.

8. The drop test device of claim 7, wherein a first conjunction rod is connected to an end of the fourth connection member, a plurality of screw threads are defined on the first conjunction rod; and the support member comprises a triangular pyramid which comprises an apex, the triangle base is located on the triangular pyramid, a second conjunction rod is connected to the apex, the second conjunction rod defines a screw hole, and the first conjunction rod is rotatably mounted in the screw hole.

* * * * *